(12) United States Patent
Soldato

(10) Patent No.: US 6,410,791 B1
(45) Date of Patent: Jun. 25, 2002

(54) NITRIC ESTERS AND NITRATE SALTS OF SPECIFIC DRUGS

(75) Inventor: Piero Del Soldato, Milan (IT)

(73) Assignee: Nicox S.A., Paris (FR)

( * ) Notice: Subject to any disclaimer, the term of this patent is extended or adjusted under 35 U.S.C. 154(b) by 0 days.

(21) Appl. No.: 09/743,808

(22) PCT Filed: Jul. 20, 1999

(86) PCT No.: PCT/EP99/05171

§ 371 (c)(1),
(2), (4) Date: Jan. 22, 2001

(87) PCT Pub. No.: WO00/06531

PCT Pub. Date: Feb. 10, 2000

(30) Foreign Application Priority Data

Jul. 28, 1998 (IT) .......................................... MI98A1743

(51) Int. Cl.[7] ...................... A61K 31/21; C07C 203/04; C07C 215/00
(52) U.S. Cl. ........................................ 564/361; 558/482
(58) Field of Search ...................... 558/482; 514/509; 564/361

(56) References Cited

FOREIGN PATENT DOCUMENTS

| GB | 2240271 A | * | 7/1991 |
| WO | WO 95/30641 | | 11/1995 |

OTHER PUBLICATIONS

Textbook of Therapeutics—Drugs and Disease Management; "Chronic Obstructive Pulmonary Disease", Goldsmith et al, 6th Ed. 1996, p. 685.

"The Anesthetized Guinea Pig as a Versatile Pharmacological Test Object", Del Soldato et al, Journal of Pharmacological Methods 5, 1981, pp. 279–285.

* cited by examiner

*Primary Examiner*—Floyd D. Higel
*Assistant Examiner*—Ebenezer Sackey
(74) *Attorney, Agent, or Firm*—Arent Fox Kintner Plotkin & Kahn

(57) ABSTRACT

A nitrate salt of a compound selected from the group consisting of: salbutamol having the formula (I)

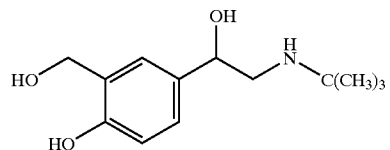

9 Claims, No Drawings

NITRIC ESTERS AND NITRATE SALTS OF SPECIFIC DRUGS

This application is a 371 of PCT/EP99/05171 filed on Jul. 20, 1999.

The present invention relates to compounds, or pharmaceutical compositions thereof, for systemic and non systemic use, to be employed in the respiratory system pathology treatment with or without infective etiopathogenetic basis, specifically chronic pulmonary diseases (chronic obstructive pulmonary diseases (COPD)), such as asthma, bronchitis, emphysema, thromboembolism with lower side effects compared with the drugs at present used for the treatment of these pathologies.

It is known in the art that for the treatment of these pathologies the most used products are Salbutamol, Salmeterol, etc. See for instance the volume "Textbook of Therapeutics —Drugs and Disease Management—6th Edition 1996" page 685. These products are effective but have the drawback to give side effects in particular towards the cardiovascular apparatus. Said products must be administered with caution to patients suffering from cardiovascular pathologies.

Other products used in these pathologies as such or as coadjuvants of other medicines are for instance Ambroxol and Bromhexine, the administration of which is accompanied also by the presence of side effects for the gastrointestinal apparatus, such as burnings and gastric sensitiveness.

The need was felt to have available compounds and their pharmaceutical compositions, effective in the treatment of respiratory system pathologies, combined with lower side effects for the cardiovascular apparatus and/or the gastrointestinal apparatus.

The Applicant has unexpectedly and surprisingly found specific compounds and compositions thereof solving the above mentioned technical problem.

It is an object of the present invention nitrate salts of compounds, or their pharmaceutical compositions, to be used for the treatment of respiratory system pathologies, specifically chronic pulmonary diseases (chronic obstructive pulmonary diseases (COPD)), such as asthma, bronchitis, emphysema, thromboembolism, infective pulmonary diseases, said compounds being characterized in that they contain at least a reactive group capable to be salified with nitric acid, said compounds being selected from the following ones:

Salbutamol having formula (I)

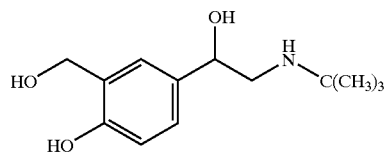

Cetrezin having formula (II)

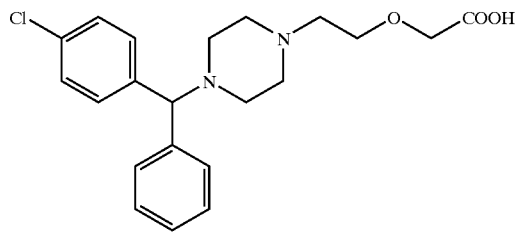

Loratadine having formula (III)

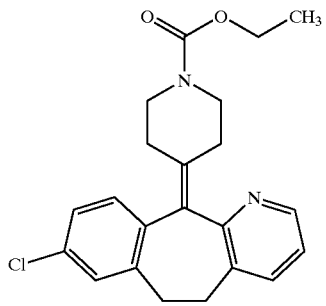

Terfenadine having formula (IV)

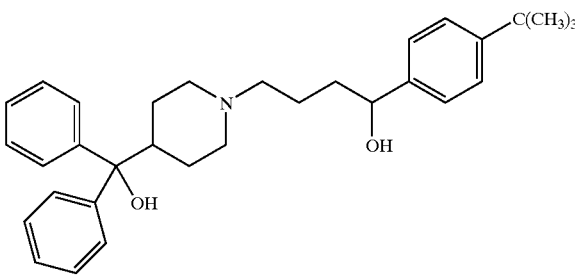

Emedasine having formula (V)

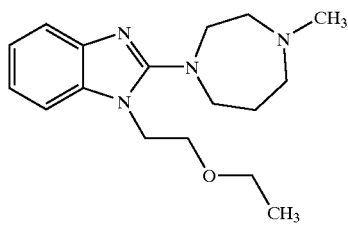

Ketoatifen having formula (VI)

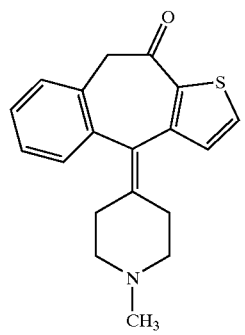

Nedocromil having formula (VII)

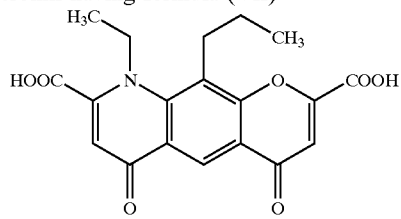

Ambroxol having formula (VIII)

Bromhexine having formula (IX)

Dextromethorphan having formula (X)

Dextrorphan having formula (XI)

Metronidazole having formula (XII)

Isoniazid having formula (XIII)

Erythromycin having formula (XIV)

Acyclovir having formula (XV)

Pyrazinamide having formula (XVI)

The preferred compounds are Salbutamol, also known as Albuterol, Cetrezin, Emedastine, Ambroxol.

The nitrate salts of the present invention can be obtained also by using the above mentioned compounds, which optionally contain one or more —$ONO_2$ groups covalently bound to the molecule by one of the following bivalent binding bridges:

YO wherein Y is a $C_1$–$C_{20}$ alkylene linear or branched when possible, preferably from 2 to 5 carbon atoms, or an optionally substituted cycloalkylene from 5 to 7 carbon atoms;

$Y_1$ selected from:

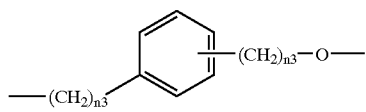

wherein $n_3$ is an integer from 0 to 3;

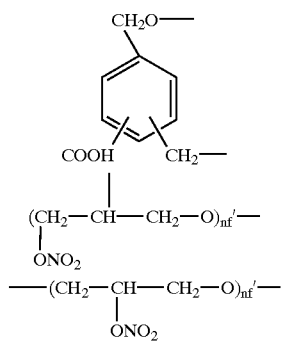

wherein nf' is an integer from 1 to 6 preferably from 2 to 4;

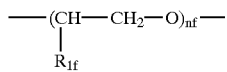

wherein $R_{1f}$=H, $CH_3$ and nf is an integer from 1 to 6; preferably from 2 to 4.

These compounds containing a —$ONO_2$ group covalently bound to the molecule by means of one of the above indicated bivalent binding bridges, are prepared as described in the patent application WO 95/30641 in the name of the Applicant, herein incorporated by reference.

In the compositions according to the present invention also one or more isomers (optical isomers included), when available, of the above described compounds, can be used.

Examples of isomers are cis-, trans-, optical isomer D and L or the racemic, enantiomer. In general one isomeric form has higher activity with respect to the other, e.g. D form with respect to L form or vice versa.

The salts of the invention contain at least one nitrate ion mole/mole of the precursor. Preferably the ratio between the moles of nitrate ion and those of the precursor is unity; salts with a higher molar ratio can be obtained when in the molecule there are other amine groups basic enough to form a ionic bond with the nitrate anion.

The salts of the present invention are formulated in the corresponding pharmaceutical compositions according to the known techniques in the field, together with the usual excipients; see for instance the "Remington's Pharmaceutical Sciences 15a Ed." volume.

The precursors of the salts belonging to the above mentioned classes are prepared according to the methods described in the Merck Index 14a Ed., herein incorporated by reference.

The salts of the present invention are obtainable according to one of the following methods.

If the precursor to be used to form the salt according to the invention is available as a free base, or as a corresponding salt, both soluble in an organic solvent preferably not containing hydroxyl groups in the molecule, such as for example acetonitrile, ethyl acetate, tetrahydrofuran, etc., the nitrate salt is prepared by dissolving the substance or its salt in said solvent at a concentration preferably equal or higher than 10% w/v, and then adding the requested amount of concentrated nitric acid, preferably diluted before addition in the same solvent used formerly to dissolve the compound, preferably cooling the mixture during and after said addition at temperatures between 20° C. and 0° C., recovering the obtained product by filtration and optionally washing the solid with the same chilled solvent.

When the precursor or its available salt are slightly soluble in the above mentioned solvent, an hydroxylated solvent is added to said solvent to improve solubility. Examples of such hydroxylated solvent are methyl alcohol, ethyl alcohol and water. Precipitation can be accelerated by diluting with an a polar solvent after nitric acid addition.

When the precursor is salified with an hydrogen halogenide, the salt with nitric acid can be prepared by adding silver nitrate to the solution of the halogenide in the above solvent. After filtering off silver halogenide, the solution is concentrated and cooled to recover the nitrate salt by precipitation.

Starting from a salt of the precursor wherein the anion is different from chloride it is however preferable to treat an aqueous solution of said salt with a saturated solution of carbonate or bicarbonate sodium or potassium salt, or with a sodium or potassium hydroxide diluted solution, then extracting the aqueous phase with a suitable organic solvent (for example halogenated solvents, esters, ethers), dehydrating and then evaporating the organic solution, dissolving the thus obtained residue in the above mentioned solvents which do not contain hydroxyl groups, e.g. acetonitrile, or in a mixture of said solvent with an hydroxylated solvent, and then following the aforementioned described preparation methods.

The salts and compositions of the present invention can be used for systemic administration, for example they can be administered by oral route, such as for expectorants; by intramuscular, intravenous route, etc.; or they can be used for non-systemic administrations, for example as aerosols or topical applications. In general the salts of the invention are used for the same therapeutical applications of the precursors.

The nitrate salts of the invention have increased general safety in the confront of the precursors.

The administered doses are those typical of the precursors; however since the products of the invention show a therapeutic effectiveness superior to that of the precursors, they can be used also at doses higher than those of the precursors without giving side effects.

Other applications of the invention products are as tokolitics (antispasmodic), for example uterine musculature antispasmodics, intestinal musculature antispasmodics; antihistamine (antiallergics) for example for ophtalmic applications; anticough, antibacterians for infective respiratory diseases. They can be administered by systemic or non systemic route, as indicated above, or also in the form of ophthalmic compositions, such as collyria, etc.

The following examples are given with the merely purpose to illustrate the invention and they are not limitative of the same.

EXAMPLE 1

Ambroxol Nitrate Salt Preparation

An Ambroxol solution (4 g, 20.6 mmoles) is prepared by dissolving it in a mixture of acetonitrile (30 ml) and tetrahydrofuran (10 ml). At low temperature (4° C.) nitric acid diluted in acetonitrile is added (3.5 ml taken from a solution obtained by adding acetonitrile to 2.7 ml of nitric acid 65% and bringing to the final volume of 10 ml with acetonitrile) After 30 minutes ethyl ether (100 ml) is slowly added, at the same temperature (+4° C.). A precipitate is formed which is filtered, washed with ethyl ether and dried under vacuum. A white amorphous solid is obtained which by the elemental analysis results to correspond to the nitrate salt of Ambroxol:

|  | C | H | N | Br |
|---|---|---|---|---|
| Calculated | 35.40% | 4.34% | 9.53% | 36.23% |
| Found | 35.37% | 4.31% | 9.57% | 36.26% |

EXAMPLE 2

Salbutamol Nitrate Salt Preparation

Starting from a Salbutamol solution (4 g, 16.7 mmoles) in acetonitrile (30 ml) and tetrahyrofuran (10 ml) and using 4 ml of nitric acid solution in acetonitrile and the same procedure of Example 1, an amorphous solid is obtained which at the elemental analysis corresponds to the nitrate salt of Salbutamol:

|  | C | H | N |
|---|---|---|---|
| Calculated | 51.65% | 7.32% | 9.27% |
| found | 51.54% | 7.38% | 9.22% |

PHARMACOLOGICAL TESTS

EXAMPLE 3

Acute Toxicity Studies of the Invention Salts

The products have been administered in suspension of carboxymethylcellulose 2% by weight to groups of 10 mice each The salt acute toxicity was evaluated by oral administration of single doses of the compounds to groups of 10 rats each, increased up to 100 mg/Kg.

The animals were kept under observation for 14 days, recording the lethality incidence and the appearance of toxic symptoms.

Also after administering of a dose of 100 mg/kg no sign of apparent toxicity has been noted.

EXAMPLE 4

Study of the Salbutamol and Nitrate Salbutamol Effects on the Experimental Bronchoconstriction in the Guinea Pig The animals were prepared according to the method of Del Soldato et Al., J. Pharmacol. Methods 5 279 1981 for the cardiorespiratory activity surveying. Each groups consisted of eight animals. 0.1 ml of a capsaicin saline solution (1 $\mu$g/Kg) was injected by intravenous route to the animals. For a total 15 minutes, starting from 5 minutes before capsaicin injection to 10 minutes after) Salbutamol (0.3 nmoles/min), or the corresponding nitrate salt (0.3 nmoles/min) or only the carrier were administered by intravenous infusion were administered to each group.

The tidal air variation before and after the capsaicin administration was measured by a Konzett apparatus modified as described in the above mentioned Del Soldato reference, connected to a polygraphic system.

The heart frequency was determined by an electrocardiographic device, according to the usual methods. The results are reported in Table 1. The average value of the heart frequency following administration of the vehicle was of 188±7 beats per minute. The responses are expressed as percent values with respect to the control.

As indicated in Table I, the Salbutamol nitrate salts results as effective as Salbutamol in inhibiting the bronchoconstrictive response induced by capsaicin, but the salt is better tolerated (no tachycardiac response) with respect to Salbutamol.

TABLE I

| Treatment | Bronchoconstriction (%) | Tachycardia (%) |
|---|---|---|
| Carrier | 100 | 100 |
| Salbutamol.HNO$_3$ | 0 | 97 |
| Salbutamol | 0 | 116 |

EXAMPLE 5

Cetirizine Nitrate Salt Preparation

The salt is prepared by adding to a solution of Cetirizine (2 g, 5.14 mmoles) in a solvent mixture made of acetonitrile (10 ml) and tetrahydrofuran (5 ml), 1.23 ml of the solution of nitric acid in acetonitrile described in example 1. An amorphous solid is obtained which at the elemental analysis corresponds to the nitrate salt of Cetirizine:

|  | C | H | N | Cl |
|---|---|---|---|---|
| Calculated | 55.81% | 5.79% | 9.29% | 7.84% |
| found | 55.84% | 5.75% | 9.22% | 7.83% |

EXAMPLE 6

Loratidine Nitrate Salt Preparation

The salt is prepared by adding to a solution of Loratidine (1 g, 2.61 mmoles) in a solvent mixture made of acetonitrile (7 ml) and tetrahydrofuran (3 ml), 0.63 ml of the solution of nitric acid in acetonitrile described in example 1. The solid obtained at the elemental analysis corresponds to the nitrate salt of Loratidine:

|  | C | H | N | Cl |
|---|---|---|---|---|
| Calculated | 59.26% | 5.42% | 9.42% | 7.95% |
| Found | 59.24% | 5.38% | 9.42% | 7.93% |

EXAMPLE 7

Terfenadine Nitrate Salt Preparation

The salt is prepared by adding to a solution of Terfenadine (1.5 g, 3.18 mmoles) in a solvent mixture made of acetonitrile (15 ml) and tetrahydrofuran (5 ml), 0.76 ml of a solution of nitric acid in acetonitrile as described in example 1. The solid obtained at the elemental analysis corresponds to the nitrate salt of Terfenadine:

|  | C | H | N |
|---|---|---|---|
| Calculated | 71.88% | 7.91% | 5.23% |
| found | 71.90% | 7.88% | 5.24% |

EXAMPLE 8

Emedastine Nitrate Salt Preparation

The salt is prepared by adding to a solution of Emedastine (2 g, 5.47 mmoles) in a solvent mixture made of acetonitrile (10 ml) and tetrahydrofuran (7 ml), 0.7 ml of the solution of nitric acid in acetonitrile described in example 1. The solid obtained at the elemental analysis corresponds to the nitrate salt of Emedastine:

|  | C | H | N |
|---|---|---|---|
| Calculated | 55.87% | 7.44% | 19.15% |
| Found | 55.84% | 7.43% | 19.18% |

EXAMPLE 9

Bromhexine Nitrate Salt Preparation

The salt is prepared by adding to a solution of Bromhexine (2 g, 5.17 mmoles) in a solvent mixture made of acetonitrile (10 ml) and tetrahydrofuran (10 ml), 1.24 ml of the solution of nitric acid in acetonitrile described in example 1. The solid obtained at the elemental analysis corresponds to the nitrate salt of Bromhexine:

|  | C | H | N | Br |
|---|---|---|---|---|
| Calculated | 38.29% | 4.81% | 12.75% | 36.39% |
| Found | 38.31% | 4.84% | 12.77% | 36.41% |

EXAMPLE 10

Dextromethorphan Nitrate Salt Preparation

The salt is prepared by adding silver nitrate (0.96 g, 5.68 mmoles) to a solution of Dextromethorphan hydrobromide (2 g, 5.68 mmoles) in acetonitrile (20 ml). The solution is then stirred at room temperature for 30 minutes. Filtering is then effected to remove silver bromide precipitate. The clear solution is added of ethyl ether (110 ml). A precipitate is formed, that is filtered, washed with ethyl ether and dried under vacuum. The solid obtained at the elemental analysis corresponds to the nitrate salt of Dextromethorphan:

|  | C | H | N |
|---|---|---|---|
| Calculated | 64.65% | 7.83% | 12.56% |
| Found | 64.68% | 7.85% | 12.54% |

EXAMPLE 11

Ketotifen Nitrate Salt Preparation

The salt is prepared by adding to a solution of Ketotifen (1 g, 3.23 mmoles) in a solvent mixture made of acetonitrile (10 ml) and tetrahydrofuran (5 ml), 0.78 ml of the solution of nitric acid in acetonitrile described in example 1. The solid obtained at the elemental analysis corresponds to the nitrate salt of Ketotifen:

|  | C | H | N | S |
|---|---|---|---|---|
| Calculated | 61.27% | 5.40% | 11.28% | 8.61% |
| Found | 61.24% | 5.43% | 11.27% | 8.60% |

EXAMPLE 12

Nedocromil Nitrate Salt Preparation

The salt is prepared by adding to a solution of Nedocromil (1 g, 2.69 mmoles) in a solvent mixture made of acetonitrile (7 ml) and tetrahydrofuran (5 ml), 0.64 ml of the solution of nitric acid in acetonitrile as described in example 1. The solid obtained at the elemental analysis corresponds to the nitrate salt of Nedocromil:

|  | C | H | N |
|---|---|---|---|
| Calculated | 52.54% | 4.17% | 9.67% |
| Found | 52.56% | 4.19% | 9.63% |

EXAMPLE 13

Dextrorphan Nitrate Salt Preparation

The salt is prepared by adding silver nitrate (0.50 g, 2.96 mmoles) to a solution of Dextrorphan hydrobromide (1 g, 2.96 mmoles) in acetonitrile (17 ml). The solution is then stirred at room temperature for 30 minutes. Filtering is then effected to remove silver bromide precipitate. The clear solution is added of ethyl ether (100 ml). A precipitate is formed, that is filtered, washed with ethyl ether and dried under vacuum. The solid obtained at the elemental analysis corresponds to the nitrate salt of Dextrorphan:

|  | C | H | N |
|---|---|---|---|
| Calculated | 63.73% | 7.54% | 13.11% |
| Found | 63.71% | 7.55% | 13.10% |

EXAMPLE 14

Antihistaminic Activity in the Guinea Pig of Cetirizine Nitrate and Cetirizine Hydrochloride— Studies on the Experimental Bronchoconstriction The animals were prepared according to the method of Del Soldato et Al., J. Pharmacol. Methods 5 279 1981 for the cardiorespiratory activity surveying. 0.1 ml of a histamine saline solution (2 $\mu g/Kg$) was injected by intravenous route to the animals. Three groups were formed, each group consisting of 8 animals. Cetirizine nitrate, Cetirizine hydrochloride, or the vehicle alone, were administered endovenously at a dose of 77 $\mu moles/\mu g$ The tidal air variation before and after the capsaicin administration was measured by a Konzett apparatus modified as described in the above mentioned Del Soldato reference, connected to a polygraphic system.

In following Table II the animal response for each treated group are expressed as percent values with respect to the control.

As indicated in the Table, the nitrate salt of Cetirizine possesses an improved antihistamine activity in the confront of Cetirizine hydrochloride.

TABLE II

| Treatment | Broncocostriction (%) |
|---|---|
| Vehicle | 100 |
| Cetirizine nitrate | 0 |
| Cetirizine hydrochloride | 40 |

EXAMPLE 15

Anti-tussive Activity in the Guinea Pig of Dextromethorphan Hydrochloride, Dextromethorphan Nitrate, Dextrorphan Hydrochloride and Dextrorphan Nitrate Guinea pigs (weight 430+20) were treated as described by Braga et Al. Arzneim. Forsch./Drug Res. 43, 550, 1993.

In this pharmacological experiment 5 groups of 8 animals each were formed. One group was not treated and was the control group.

Each animal was placed in a cylindrical glass container having one tubing through each of the two circular flat surfaces. Said tubing were, respectively, for the aerosol inlet and outlet. The outlet tubing is connected to a polygraphic system.

The aerosol was formed from a solution 7.5% by weight of citric acid in water.

The air variation inside the glass container was registered before and after a cough stroke caused by the aerosol. One hour later Dextromethorphan hydrochloride, Dextromethorphan nitrate, Dextrorphan hydrochloride and dextrorphan nitrate were i.p. administered in a physiologic solution at a dose of 110 micromoles/Kg. 30 minutes after the injection the animals were treated with the aerosol. It was then registered the number of cough strokes for a time of 10 minutes. In the following Table III are reported the average response obtained from each treated group, referred to that of the control group, made 100%.

TABLE III

| Treatment | cough strokes (%) |
|---|---|
| Vehicle | 100 |
| Dextromethorphan nitrate | 0 |
| Dextromethorphan hydrochloride | 30 |
| Dextrorphan nitrate | 0 |
| Dextrorphan hydrochloride | 40 |

As shown in the Table, the nitrate salts of Dextromethorphan and Dextrorphan are more potent antitussive agents than the corresponding hydrochlorides.

EXAMPLE 16

Mucolitic Activity in Mice of Ambroxol Nitrate and Ambroxol Hydrochloride

Mucolitic activity in male mice was evaluated according to the Method of Engler and Zselenyi, J. Pharm. Methods 11, 151, 1984. By this method it is determined the quantity of phenol red in the tracheal secretion. The animals were previously administered i.p. at a dose of 500 mg/Kg with the dye dissolved in physiologic solution. 3 groups of mice (weight 18±2 g), of 10 animal each, were treated i.p. with the dye. One group was the control group. Each of the two treated groups received, ten minutes before the above injection, an i.p. injection of 264 micromoles/Kg of Ambroxol nitrate or Ambroxol hydrochloride, respectively. 30 minutes after the phenol red injection, the animals were sacrificed. The trachea was freed from the surrounding tissues, dissected and washed for 30 minutes in 3 ml of physiologic solution. 0.1 ml of 1 M sodium hydroxide were then added to the physiologic solution. The washings were centrifuged for 15 minutes at 3000 rpm. A spectrophotometric assay was performed on the supernatant in order to determine the concentration of phenol red in the physiologic solution. Mucolitic activity was determined as % variation of absorbance of the sample in the confront of that of the control group, assumed to be 100%.

Table IV resumes the results obtained.

TABLE IV

| Treatment | Mucolitic activity (%) |
|---|---|
| Vehicle | 100 |
| Ambroxol nitrate | 0 |
| Ambroxol hydrochloride | 30 |

The table shows that the mucolitic activity of the (Ambroxol nitrate salt is higher than that of the corresponding hydrochloride.

EXAMPLE 17

Metronidazole Nitrate Salt Preparation

The salt is prepared by adding to a solution of Metronidazole (1 g, 5.84 mmoles) in a solvent mixture made of acetonitrile (8 ml) and tetrahydrofuran (5 ml), 1.40 ml of the solution of nitric acid in acetonitrile described in example 1. The solid obtained at the elemental analysis corresponds to the nitrate salt of Metronidazole:

| | C | H | N |
|---|---|---|---|
| Calculated | 30.77% | 4.30% | 24.03% |
| Found | 30.74% | 4.28% | 24.00% |

EXAMPLE 8

Isoniazid Nitrate Salt Preparation

The salt is prepared by adding to a solution of Isoniazid (2 g, 14.58 mmoles) in a solvent mixture made of acetonitrile (20 ml) and tetrahydrofuran (10 ml), 3.50 ml of the solution of nitric acid in acetonitrile described in example 1. The solid obtained at the elemental analysis corresponds to the nitrate salt of Isoniazid:

| | C | H | N |
|---|---|---|---|
| Calculated | 36.00% | 4.02% | 27.99% |
| Found | 35.97% | 4.00% | 28.01% |

EXAMPLE 19

Erythromycin Nitrate Salt Preparation

The salt is prepared by adding to a solution of Erythromycin (2 g, 2.72 mmoles) in a solvent mixture made of acetonitrile (23 ml) and tetrahydrofuran (17 ml), 0.65 ml of the solution of nitric acid in acetonitrile described in example 1. The solid obtained at the elemental analysis corresponds to the nitrate salt of Erythromycin:

|  | C | H | N |
|---|---|---|---|
| Calculated | 57.72% | 8.89% | 3.63% |
| Found | 57.75% | 8.90% | 3.65% |

EXAMPLE 20

Acyclovir Nitrate Salt Preparation

The salt is prepared by adding to a solution of Acyclovir (1 g, 4.44 mmoles) in a solvent mixture made of acetonitrile (10 ml) and tetrahydrofuran (10 ml), 1.06 ml of the solution of nitric acid in acetonitrile described in example 1. The solid obtained at the elemental analysis corresponds to the nitrate salt of Acyclovir:

|  | C | H | N |
|---|---|---|---|
| Calculated | 33.33% | 4.19% | 29.17% |
| Found | 33.30% | 4.20% | 29.18% |

EXAMPLE 21

Pyrazinamide Nitrate Salt Preparation

The salt is prepared by adding to a solution of Pyrazinamide (1 g, 8.12 mmoles) in a solvent mixture made of acetonitrile (10 ml) and tetrahydrofuran (10 ml), 1.95 ml of the solution of nitric acid in acetonitrile described in example 1. The solid obtained at the elemental analysis corresponds to the nitrate salt of Pyrazinamide:

|  | C | H | N |
|---|---|---|---|
| Calculated | 48.78% | 3.25% | 30.10% |
| Found | 48.80% | 3.24% | 30.13% |

What is claimed is:

1. A nitrate salt of a compound selected from the group consisting of:
salbutamol having the formula (I)

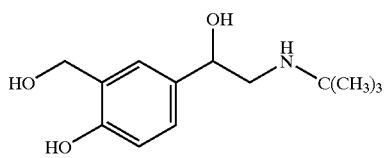

2. The nitrate salt according to claim 1, wherein the compound contains one —$ONO_2$ group covalently bound to the molecule by one of the following bivalent binding bridges:

YO wherein Y is a $C_1$–$C_{20}$ alkylene linear or branched, or a substituted or unsubstituted cycloalkylene from 5 to 7 carbon atoms;

$Y_1$ selected from:

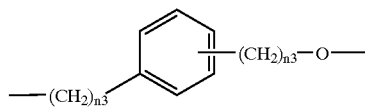

wherein $n_3$ is an integer from 0 to 3;

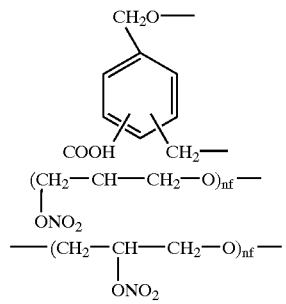

wherein nf' is an integer from 1 to 6;

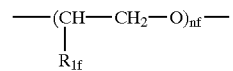

wherein $R_{1f}$=H, $CH_3$ and nf is an integer from 1 to 6.

3. The nitrate salt according to claim 1 containing at least one isomer of salbutamol.

4. A pharmaceutical composition of the nitrate salt according to claim 1.

5. A medicine comprising the nitrate salt according to claim 1.

6. A method for the treatment of respiratory system pathologies, said method comprising administering to a patient an effective amount of a medicine comprising the nitrate salt or composition according to claim 5.

7. A method for the treatment of spasms, said method comprising administering to a patient an effective amount of a tokolitic comprising the nitrate salt or composition according to claim 5.

8. A method for the treatment of allergies, said method comprising administering to a patient an effective amount of an antiallergic comprising the nitrate salt or composition according to claim 5.

9. A method for the treatment of respiratory system pathologies, said method comprising administering to a patient an effective amount of a medicine comprising the nitrate salt according to claim 1.

* * * * *